(12) United States Patent
Madsen et al.

(10) Patent No.: US 11,731,371 B2
(45) Date of Patent: Aug. 22, 2023

(54) STERILE CONNECTION OF TUBING

(71) Applicant: Fenwal, Inc., Lake Zurich, IL (US)

(72) Inventors: James Madsen, Chicago, IL (US);
Kyungyoon Min, Kildeer, IL (US);
Mark J. Brierton, Cary, IL (US); Tom Westberg, Lake Forest, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 17/580,684

(22) Filed: Jan. 21, 2022

(65) Prior Publication Data

US 2022/0234303 A1 Jul. 28, 2022

Related U.S. Application Data

(60) Provisional application No. 63/140,995, filed on Jan. 25, 2021.

(51) Int. Cl.
*B29C 65/74* (2006.01)
*B29C 65/18* (2006.01)
(Continued)

(52) U.S. Cl.
CPC ............ *B29C 65/743* (2013.01); *B29C 65/18* (2013.01); *B29C 66/5221* (2013.01);
(Continued)

(58) Field of Classification Search
CPC ... B29C 65/18; B29C 65/743; B29C 66/5221; B29C 66/857; B29C 66/91421; B29C 66/9261; F16L 47/02
See application file for complete search history.

(56) References Cited

U.S. PATENT DOCUMENTS 4,157,723 A 6/1979 Granzow et al.
4,369,779 A * 1/1983 Spencer .............. B29C 66/7373
604/905

(Continued)

FOREIGN PATENT DOCUMENTS

EP 0044204 A2 1/1982
EP 1469905 B1 10/2004
(Continued)

OTHER PUBLICATIONS

Extended European Search Report, dated Jul. 4, 2022, for application No. EP22152594.2-1122.

*Primary Examiner* — George R Koch
(74) *Attorney, Agent, or Firm* — Cook Alex Ltd.

(57) ABSTRACT

A sterile connection device includes first and second carriages. The first carriage defines a first portion of a proximal slot and a first portion of a distal slot, while the second carriage defines second portions of the proximal and distal slots. A controller executes a sterile connection procedure in which a solid cutting blade is heated, followed by the heated blade being moved to a cutting position to cut sealed proximal and distal tubes received by the slots. The second carriage moves proximally or distally with respect to the first carriage so as to align the cut ends of the tubes. The heated blade then moves out of the cutting position, followed by the first carriage moving toward the second carriage so as to press the cut ends of the tubes into contact with each other so as to sterilely connect the cut ends and define a joined tube.

20 Claims, 10 Drawing Sheets

(51) Int. Cl.
*B29C 65/00* (2006.01)
*F16L 47/02* (2006.01)
*G05D 23/22* (2006.01)
*A61M 39/18* (2006.01)
*B29L 31/00* (2006.01)

(52) U.S. Cl.
CPC ...... *B29C 66/857* (2013.01); *B29C 66/91421* (2013.01); *B29C 66/9261* (2013.01); *F16L 47/02* (2013.01); *G05D 23/22* (2013.01); *A61M 39/18* (2013.01); *B29L 2031/753* (2013.01)

(56) References Cited

U.S. PATENT DOCUMENTS

| | | | |
|---|---|---|---|
| 4,412,835 A | 11/1983 | Spencer | |
| 4,443,215 A | 4/1984 | Smith | |
| 4,476,631 A | 10/1984 | Benin | |
| 4,501,951 A | 2/1985 | Benin et al. | |
| 4,507,119 A | 3/1985 | Spencer | |
| 4,516,971 A | 5/1985 | Spencer | |
| 4,521,263 A | 6/1985 | Benin et al. | |
| 4,610,670 A * | 9/1986 | Spencer | B29C 65/203 604/905 |
| 4,619,642 A | 10/1986 | Spencer | |
| 4,633,063 A | 12/1986 | Willis | |
| 4,647,756 A | 3/1987 | Willis | |
| 4,737,214 A | 4/1988 | Leurink et al. | |
| 4,753,697 A | 6/1988 | Shaposka et al. | |
| 4,770,735 A | 9/1988 | Shaposka et al. | |
| 4,793,880 A | 12/1988 | Shaposka et al. | |
| 4,832,773 A | 5/1989 | Shaposka et al. | |
| 4,864,101 A | 9/1989 | Shaposka et al. | |
| 4,897,138 A | 1/1990 | Shaposka et al. | |
| 4,913,756 A | 4/1990 | Shaposka et al. | |
| 4,933,036 A | 6/1990 | Shaposka et al. | |
| 4,978,446 A | 12/1990 | Lobdell | |
| 5,141,592 A | 8/1992 | Shaposka et al. | |
| D329,500 S | 9/1992 | Arioka et al. | |
| 5,156,701 A | 10/1992 | Spencer et al. | |
| 5,158,630 A | 10/1992 | Shaposka et al. | |
| 5,209,800 A | 5/1993 | Spencer et al. | |
| 5,244,522 A | 9/1993 | Spencer | |
| 5,248,359 A | 9/1993 | Shaposka et al. | |
| 5,256,229 A | 10/1993 | Spencer | |
| 5,279,685 A | 1/1994 | Ivansons et al. | |
| D353,465 S | 12/1994 | Arioka et al. | |
| D355,848 S | 2/1995 | Ivansons et al. | |
| 5,397,425 A | 3/1995 | Ivansons et al. | |
| D357,926 S | 5/1995 | Ivansons et al. | |
| 5,502,293 A | 3/1996 | Ohnishi et al. | |
| 5,518,575 A | 5/1996 | Watanabe | |
| 5,525,186 A | 6/1996 | Ivansons et al. | |
| 5,632,852 A | 5/1997 | Ivansons et al. | |
| 5,674,333 A | 10/1997 | Spencer | |
| 5,802,689 A | 9/1998 | Sano | |
| 5,855,731 A | 1/1999 | Spencer | |
| 5,871,612 A | 2/1999 | Spencer | |
| 6,020,574 A | 2/2000 | Ivansons | |
| 6,026,882 A | 2/2000 | Yamada et al. | |
| 6,177,652 B1 | 1/2001 | Ivansons | |
| 6,341,637 B1 | 1/2002 | Yamada et al. | |
| 6,460,592 B1 | 10/2002 | Sano et al. | |
| 6,463,979 B1 | 10/2002 | Sano et al. | |
| 6,485,593 B1 | 11/2002 | Christoffersen | |
| 6,635,324 B1 | 10/2003 | Wolfe, Jr. et al. | |
| 6,637,489 B1 | 10/2003 | Spencer | |
| 6,705,372 B2 | 3/2004 | Sano et al. | |
| 6,913,056 B2 | 7/2005 | Landherr et al. | |
| D528,137 S | 9/2006 | Huang | |
| 7,119,305 B2 | 10/2006 | Sano et al. | |
| 7,122,094 B2 | 10/2006 | Baradon et al. | |
| 7,226,649 B2 | 6/2007 | Shang et al. | |
| 7,371,305 B2 | 5/2008 | Sano et al. | |
| 7,398,813 B1 | 7/2008 | Ivansons et al. | |
| 7,459,054 B2 | 12/2008 | Landherr et al. | |
| 7,657,996 B2 | 2/2010 | Sano et al. | |
| 7,779,880 B2 | 8/2010 | Sano et al. | |
| 7,922,848 B2 | 4/2011 | Ishida et al. | |
| 8,066,269 B2 | 11/2011 | Ivansons et al. | |
| 8,146,642 B2 | 4/2012 | Landherr et al. | |
| D665,434 S | 8/2012 | Mueller et al. | |
| 8,708,019 B2 | 4/2014 | Ivansons et al. | |
| 8,857,485 B2 | 10/2014 | Buhler et al. | |
| 8,863,364 B2 | 10/2014 | Gay et al. | |
| 8,910,918 B2 | 12/2014 | Gay et al. | |
| 9,205,612 B2 | 12/2015 | Ivansons et al. | |
| 9,505,168 B2 | 11/2016 | Hinterseer | |
| 9,950,469 B2 | 4/2018 | Ivansons et al. | |
| 10,029,088 B2 | 7/2018 | He | |
| 10,040,247 B2 | 8/2018 | Schwalm et al. | |
| 10,081,135 B2 | 9/2018 | Patil et al. | |
| 10,195,416 B2 | 2/2019 | Gebauer et al. | |
| 10,307,582 B2 | 6/2019 | Wegener et al. | |
| 10,183,447 B2 | 9/2019 | Chengalvarayan et al. | |
| 10,532,115 B2 | 1/2020 | Mosdzianowski et al. | |
| 10,569,475 B2 | 2/2020 | Cassiday et al. | |
| 10,864,685 B2 | 12/2020 | Kanemaru | |
| 11,077,623 B2 | 8/2021 | Buhler et al. | |
| 11,103,688 B2 | 8/2021 | Demizu et al. | |
| 2003/0143352 A1 | 7/2003 | Yang et al. | |
| 2017/0276281 A1 | 9/2017 | Schwalm et al. | |
| 2018/0345589 A1 | 12/2018 | Buhler et al. | |
| 2020/0047422 A1* | 2/2020 | Kanemaru | B29C 66/8167 |
| 2020/0047423 A1 | 2/2020 | Kanemaru | |

FOREIGN PATENT DOCUMENTS

| | | |
|---|---|---|
| EP | 3221121 A1 | 9/2017 |
| EP | 3597232 A1 | 1/2020 |
| WO | WO 92/05945 A2 | 4/1992 |
| WO | WO 2005/000565 A1 | 1/2005 |
| WO | WO 2014/128972 A1 | 8/2014 |
| WO | WO 2019/021530 A1 | 1/2019 |
| WO | WO 2021/188049 A1 | 9/2021 |

* cited by examiner

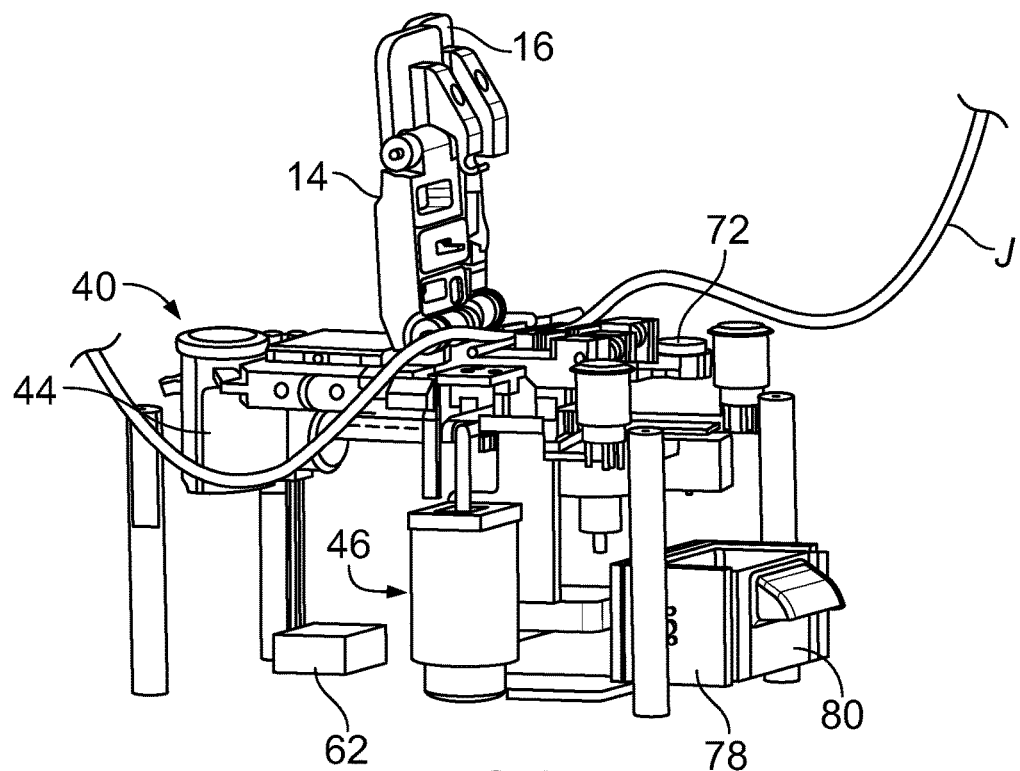
FIG. 6
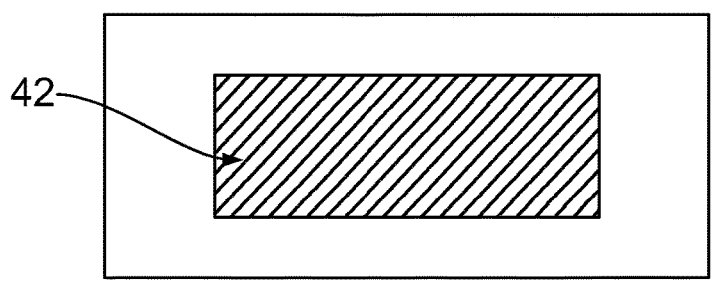
FIG. 7
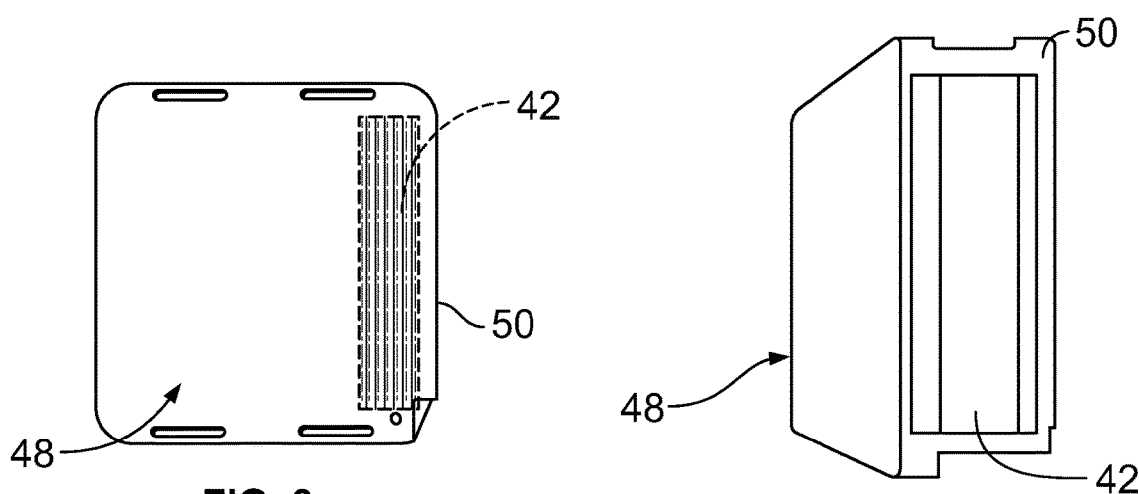
FIG. 8
FIG. 9

STERILE CONNECTION OF TUBING

CROSS-REFERENCE TO RELATED APPLICATIONS

This application claims the benefit of and priority of U.S. Provisional Patent Application Ser. No. 63/140,995, filed Jan. 25, 2021, the contents of which are incorporated by reference herein.

BACKGROUND

Field of the Disclosure

The invention relates to joinder of tubing. More particularly, the invention relates to systems and methods for sterilely joining tubing.

Description of Related Art

Fluid flow systems or assemblies that are pre-sterilized and/or pre-assembled are used in a wide variety of medical and non-medical applications. Medical applications may include, for example, administration of medical fluids to a patient for therapeutic and/or diagnostic purposes, blood and/or blood component or other cell collection or processing, dialysis, and other medical procedures. Non-medical applications for such systems or assemblies may include, for example, pharmaceutical manufacturing and cell processing. In the medical field in particular, such flow systems commonly employ one or more pre-filled containers or other sources of medical fluid or agent and an associated fluid flow circuit or system (sometimes called a tubing set) containing the necessary flow tubing, valves, flow controllers, process chambers, and the like to carry out the particular procedure, either alone or in cooperation with a reusable controller or other device. It is not unusual, for example, for a medical fluid flow system to include or be used in association with a container of a suitable drug, saline, anticoagulant, dextrose solution, sterile water, cell preservative, or the like, to name just a few examples.

Such a fluid flow system can, however, pose manufacturing or assembly challenges for different reasons. One reason can be that the pre-filled containers of medical liquid, powder, or other agent that is administered to the patient or otherwise employed in the medical fluid flow system, require different sterilization techniques than other portions of the fluid flow system. For example, empty plastic tubing, containers, flow control devices, and/or processing devices or chambers, which do not contain any substantial amount of liquid or other agent, may be sterilized with gamma or electron beam (e-beam) radiation or by exposure to a sterilizing gas, e.g., ethylene oxide. However, gas sterilization would be ineffective to sterilize an agent, such as a liquid, powder, or drug, contained in a sealed container, and exposing the agent to ionizing radiation may degrade or otherwise have a deleterious effect on the agent. Also, there may be situations where different portions of a sterile fluid flow system, even though suitable for the same sterilization process, are separately manufactured and sterilized for other reasons and then subsequently assembled in a sterile manner.

In addition, sterile connections often need to be made on-site, by the end user, e.g., at the location where the fluid flow systems are being used to treat patients or collect or process blood or blood components or biologic materials, or in other therapeutic or diagnostic procedures. As a result, a number of different approaches have been used in assembling sterile fluid flow systems. For example, one technique for manufacturing such systems employs the use of a sterile docking system, such as a device disclosed in U.S. Pat. No. 4,157,723, which is hereby incorporated herein by reference. As illustrated therein, the sterile docking system comprises a pair of mating members, each having a facing membrane. One of the mating members is connected to a pre-sterilized container of liquid, drug or other agent and the other mating member is attached to a pre-sterilized fluid flow system, which may include one or more empty containers. After the two members are joined, the docking system is exposed to radiant energy, causing the membranes to melt and form a sterile fluid pathway through the mating members. Fluid may then be transferred from the initial container into an empty container in the fluid flow system, and the flow path sealed and severed. The initial container and mating members are then discarded. While this works satisfactorily, it entails multiple manufacturing steps of transferring solution from one container to another in a sterile manner and the associated quality control procedures with such a step. It also requires the disposal of a portion of the product with increased product and waste cost.

According to an alternative approach, which is described in U.S. Pat. No. 4,978,446 (which is hereby incorporated herein by reference), sterilizing filters are used on the inlet flow line that couples a pre-sterilized liquid container or the like to a separately sterilized fluid flow tubing system. In this approach, medical personnel are required to manually join the fluid flow tubing system to the fluid container, such as by spiking the fluid container with a piercing member associated with the fluid flow system. In addition to the administrative requirements for individually ordering, storing, and prescribing solutions and disposable flow systems or sets, there is the added possibility of errors, such as by connection of a container of an incorrect liquid or other agent or an improper flow system to be used in association with the procedure.

Also, there are known devices commonly referred to as a sterile tubing welder, with the device marketed by Terumo Medical Corporation as the TSCD-II sterile tubing welder being one example. That device uses a heated cutting element to slice and melt the ends of tubing, which are joined together after the cutting element is removed. Aspects of this device are disclosed in U.S. Patent Application Publication No. 2020/0047423, which is hereby incorporated herein by reference. One notable disadvantage of this device is that it requires the use of expensive cutting elements (each comprising a resistive circuit layer sandwiched between two copper layers) that are replaced after each splice.

Accordingly, there remains a need for advancements in this field.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a sterile connection device includes a housing and first and second carriages. The first carriage includes a lower jaw defining a first portion of a proximal slot configured to receive a portion of a proximal sealed tube and defining a first portion of a distal slot configured to receive a portion of a distal sealed tube. The first carriage also includes an upper jaw configured to move between an open condition spaced away from the lower jaw and a closed condition positioned adjacent to the lower jaw. The second carriage is positioned laterally of the first carriage and includes a lower jaw defining a second portion of the proximal slot and a second portion of the distal slot, with an upper jaw that is configured to move between an open condition spaced away from the lower jaw and a closed condition positioned adjacent to the lower jaw. The sterile connection device further includes a blade handling assembly, a blade heating assembly, and a system controller. The system controller is configured to execute a sterile connection procedure when proximal and distal tubes are received by the proximal and distal slots and the upper jaws are in their closed conditions. The procedure includes controlling the blade heating assembly to heat the solid cutting blade by conductive heating, controlling the blade handling assembly to move the heated blade to a cutting position so as to cut the proximal and distal tubes, and controlling the second carriage to move proximally or distally with respect to the first carriage so as to align one of the portions of the proximal slot with one of the portions of the distal slot. The system controller then controls the blade handling assembly to advance the heated blade out of the cutting position, followed by controlling the first carriage to move laterally toward the second carriage so as to press cut ends of the proximal and distal tubes received by the aligned portions of the proximal and distal slots into contact with each other so as to sterilely connect the cut ends and define a joined tube.

In another aspect, a sterile connection device includes a housing and first and second carriages. The first carriage includes a lower jaw defining a first portion of a proximal slot configured to receive a portion of a proximal sealed tube and defining a first portion of a distal slot configured to receive a portion of a distal sealed tube. The first carriage also includes an upper jaw configured to move between an open condition spaced away from the lower jaw and a closed condition positioned adjacent to the lower jaw. The second carriage is positioned laterally of the first carriage and includes a lower jaw defining a second portion of the proximal slot and a second portion of the distal slot, with an upper jaw that is configured to move between an open condition spaced away from the lower jaw and a closed condition positioned adjacent to the lower jaw. The sterile connection device further includes a blade handling assembly, a blade heating assembly, and a system controller. The system controller is configured to execute a sterile connection procedure when proximal and distal tubes are received by the proximal and distal slots and the upper jaws are in their closed conditions. The procedure includes controlling the blade heating assembly to heat the solid cutting blade using a ceramic heating element, controlling the blade handling assembly to move the heated blade to a cutting position so as to cut the proximal and distal tubes, and controlling the second carriage to move proximally or distally with respect to the first carriage so as to align one of the portions of the proximal slot with one of the portions of the distal slot. The system controller then controls the blade handling assembly to advance the heated blade out of the cutting position, followed by controlling the first carriage to move laterally toward the second carriage so as to press cut ends of the proximal and distal tubes received by the aligned portions of the proximal and distal slots into contact with each other so as to sterilely connect the cut ends and define a joined tube.

BRIEF DESCRIPTION OF THE DRAWINGS

FIGS. 4-6 are perspective views of the sterile connect device of FIG. 1, with various portions thereof broken away or omitted for illustrative purposes;

FIG. 7 is a top plan view of a disposable blade used in combination with the sterile connect device of FIG. 1;

FIG. 8 is a side elevational view of a blade cartridge configured for dispensing blades of the type shown in FIG. 7;

FIG. 9 is a perspective view of the blade cartridge of FIG. 8;

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
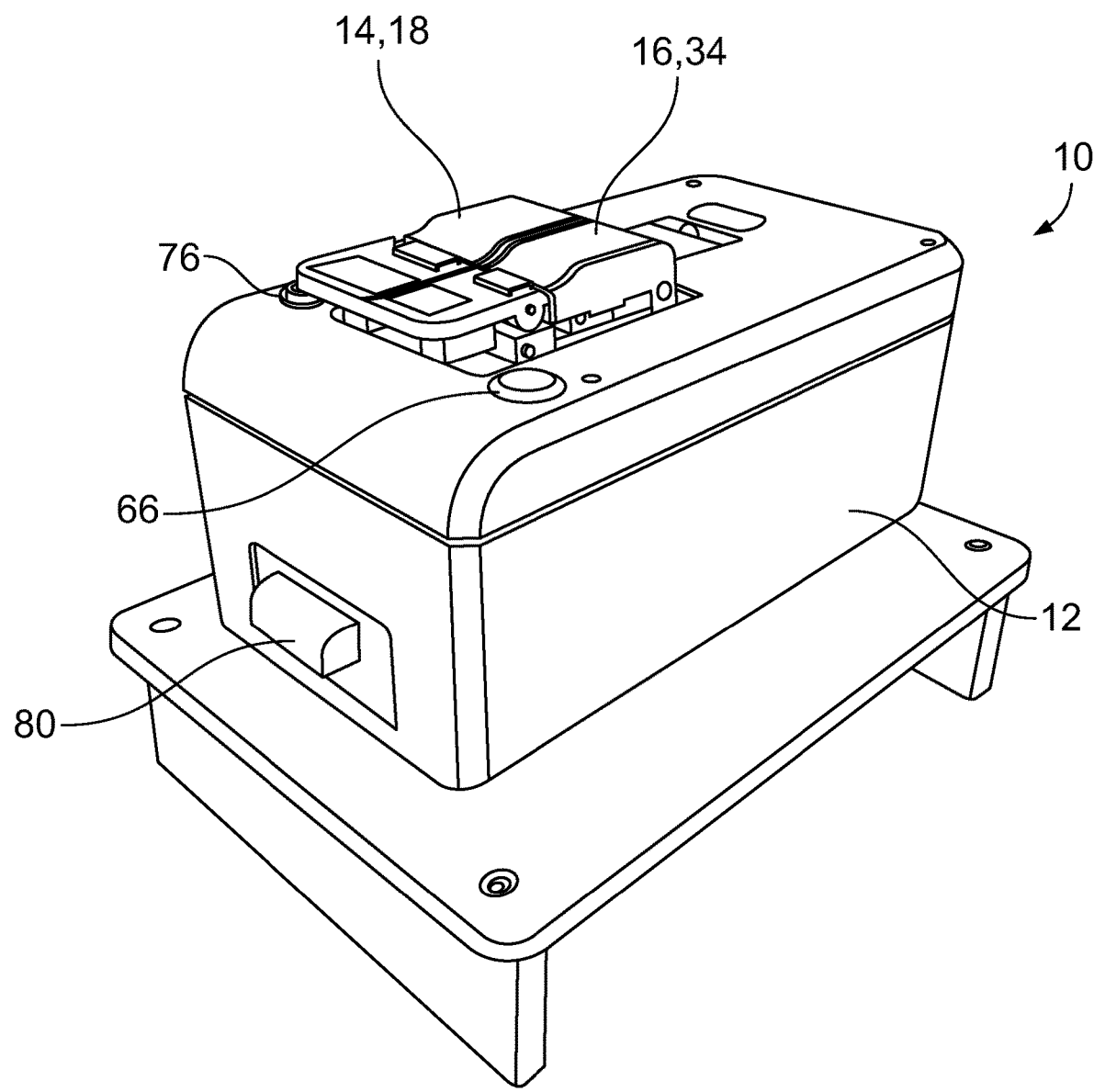
FIG. 1 is a perspective view of a sterile connection device according to an aspect of the present disclosure, with upper jaws of the device in a closed condition.
Figure 2:
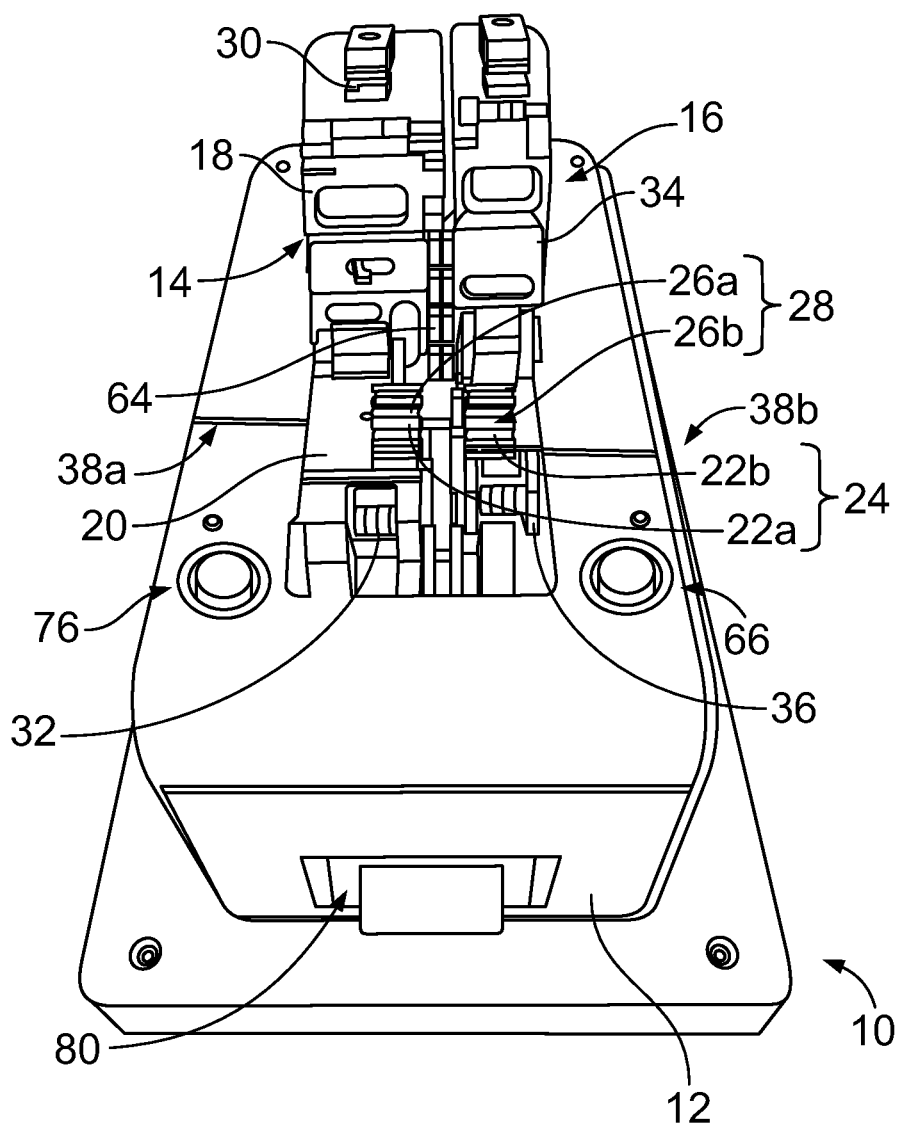
FIGS. 2 and 3 are perspective views of the sterile connect device of FIG. 1, with upper jaws of the device in an open condition.
Figure 3:
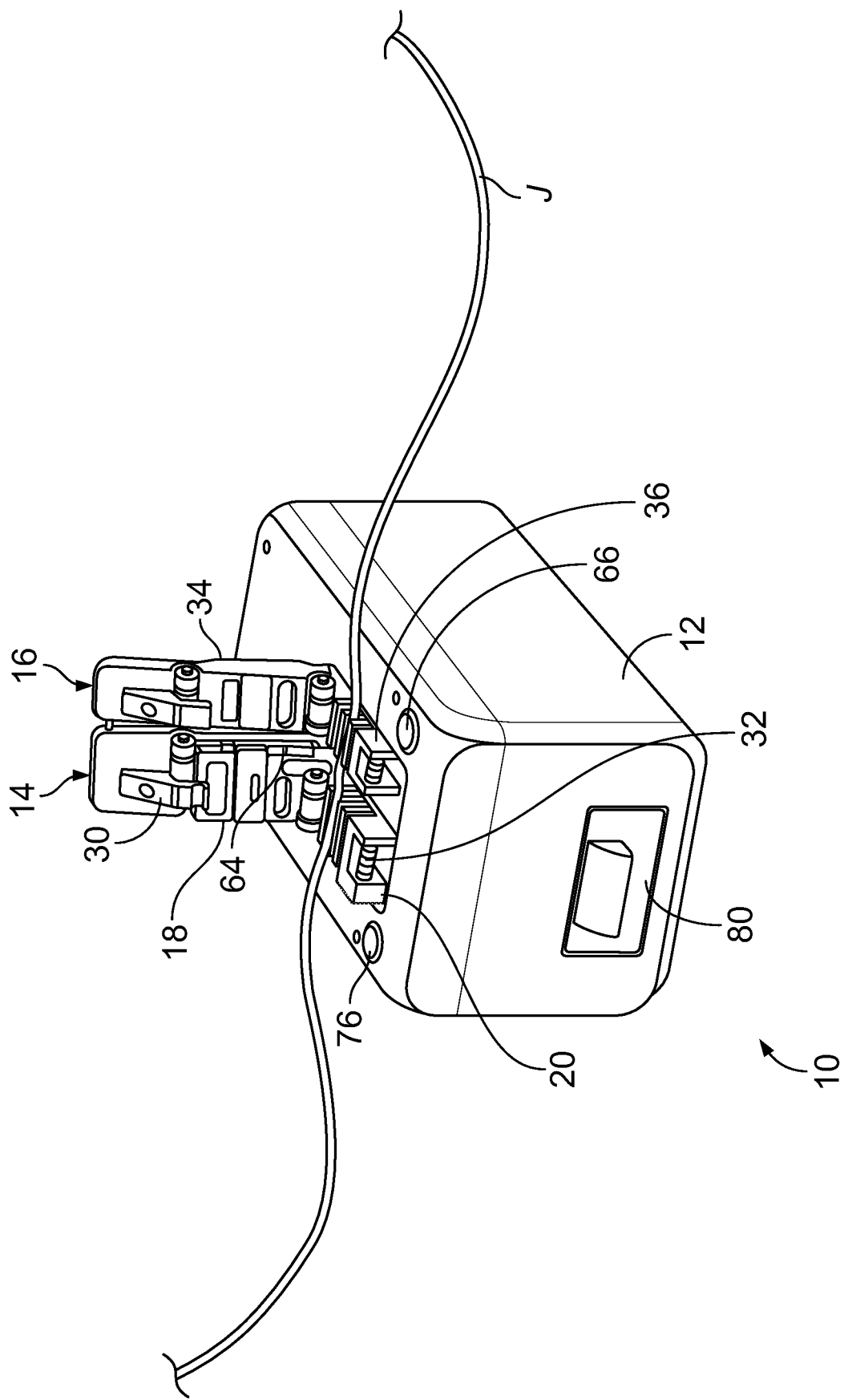
Figure 4:
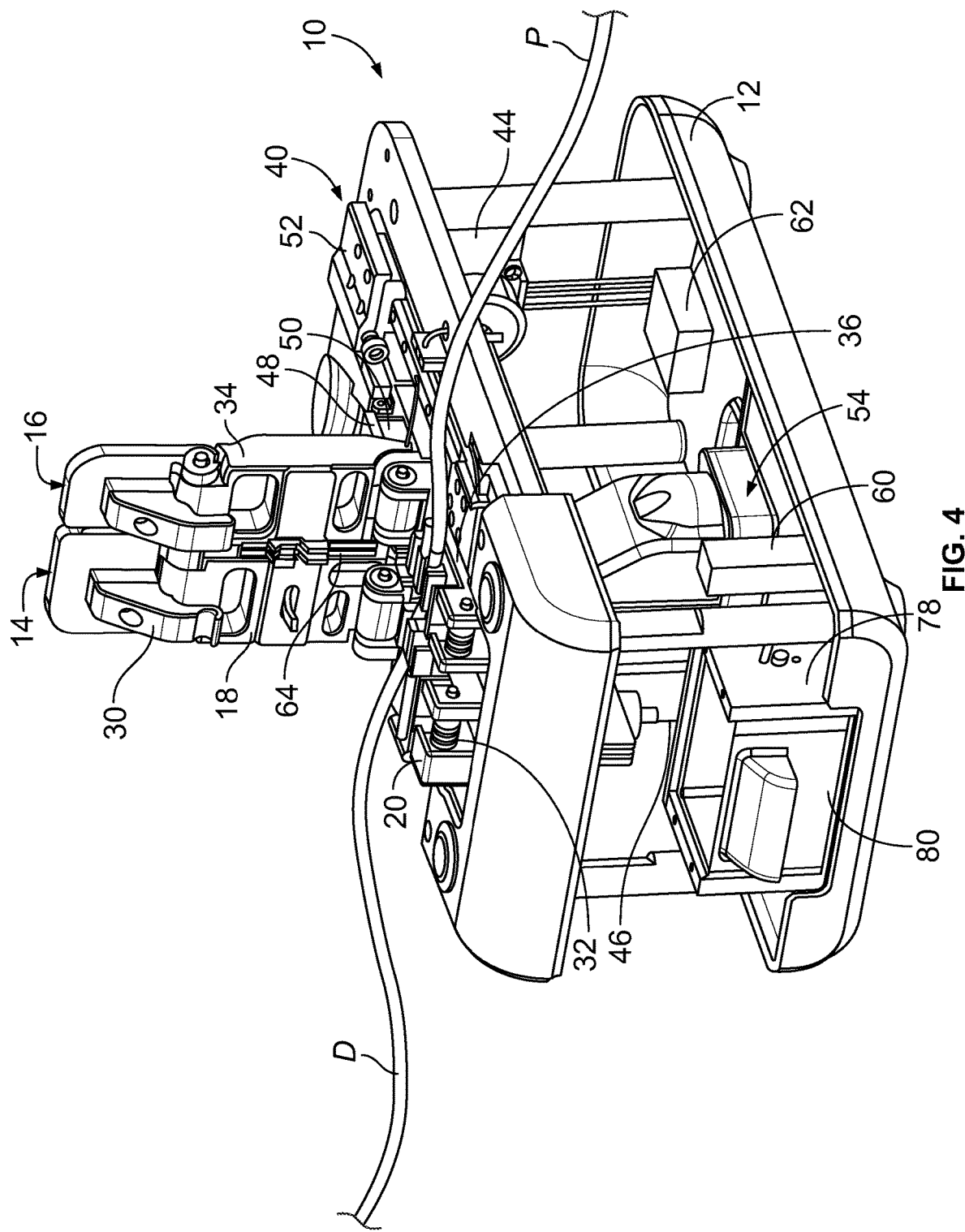
Figure 5:
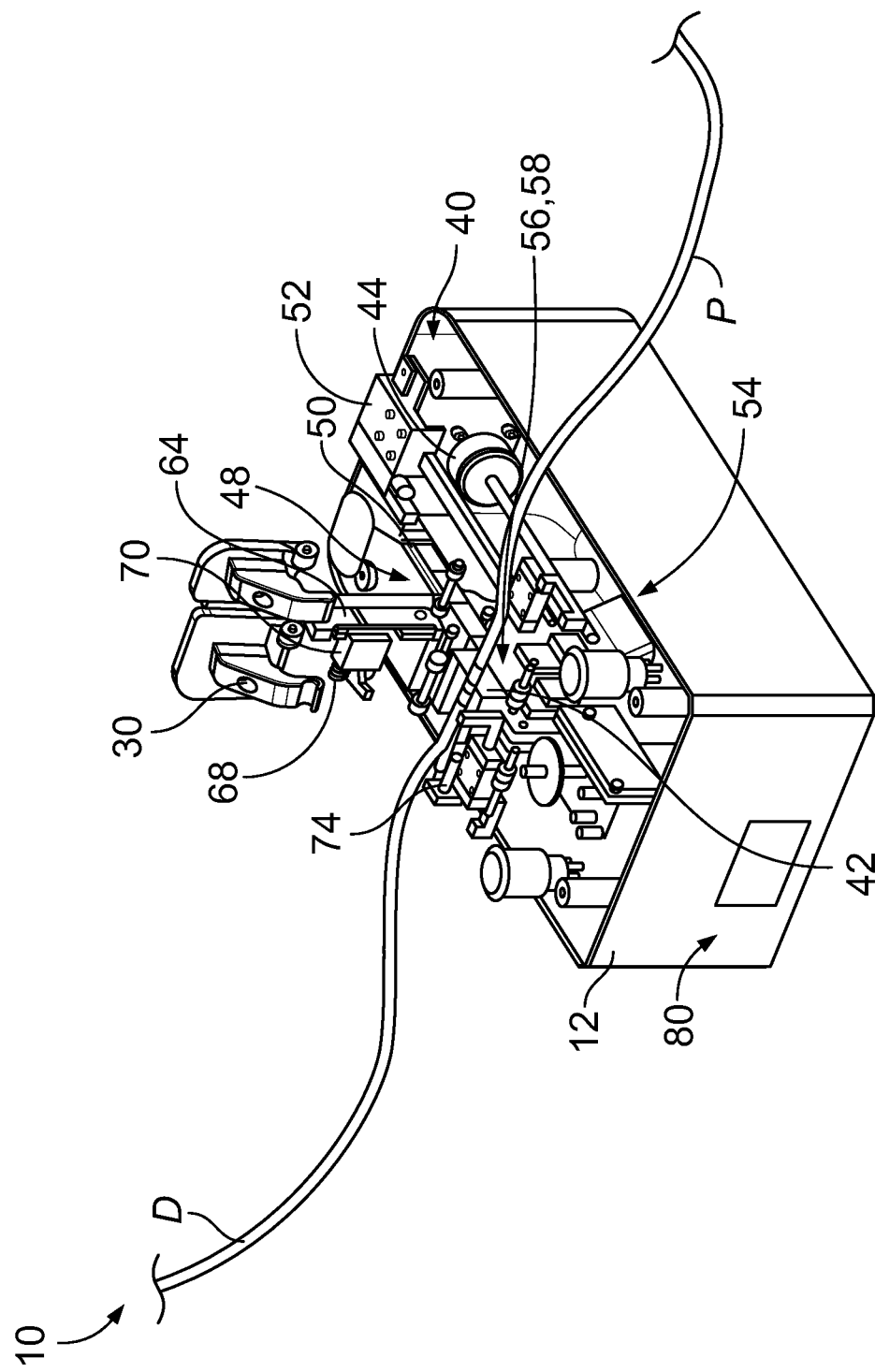

FIGS. 1-3 illustrate an exemplary embodiment of a sterile connection device 10 according to an aspect of the present disclosure, while FIGS. 4-6 illustrate the sterile connection device 10 with assorted portions thereof broken away or omitted for illustrative purposes. While sterile connection devices according to the present disclosure are particularly well-suited for sterile connection of tubes formed of polyvinyl chloride, it is within the scope of the present disclosure for the sterile connection device 10 to be used to sterilely connect tubes formed of other materials.

The illustrated sterile connection device 10 includes a housing 12 containing the various components of the sterile connection device 12. The housing 12 may be variously configured without departing from the scope of the present disclosure, which may include the housing 12 having different portions being formed of, for example, a metallic material, a plastic material, or a combination of metallic and plastic materials.

In the illustrated embodiment, first and second carriages 14 and 16 are associated with an upper surface or face of the housing 12, with the second carriage 16 being positioned laterally of the first carriage 14. At least a portion of at least one of (but more preferably both of) the carriages 14, 16 is movable with respect to the housing 12 during a sterile connection procedure in which two sealed tubes "P" and "D" (FIG. 4) are joined together. The first carriage 14 includes an upper jaw 18 and a lower jaw 20, with the upper jaw 18 being movable between a closed condition (FIG. 1) and an open condition (FIGS. 2-4). The upper jaw 18 of the illustrated embodiment is pivotal between the closed and open conditions, but it should be understood that the upper jaw 18 may be otherwise movable between the closed and open conditions (e.g., via vertical translational movement) without departing from the scope of the present disclosure.

When the upper jaw 18 is in the open condition, the lower jaw 20 is exposed or uncovered, which allows a pair of sealed tubes P and D to be mounted within the first carriage 14 (at the beginning of a sterile connection procedure) and allows for a joined tube "J" (FIGS. 3 and 6) to be removed from the first carriage 14 (at the end of a sterile connection procedure). The lower jaw 20 of the first carriage 14 defines a first portion 22a of a proximal slot 24 and a first portion 26a of a distal slot 28 that is parallel to the first portion 22a of the proximal slot 24 (FIG. 2). In the illustrated embodiment, the first portions 22a and 26a of the proximal and distal slots 24 and 28 are substantially identical, but it should be understood that they may be differently configured without departing from the scope of the present disclosure. Regardless of their exact configuration, each of the first portions 22a, 26a is sized and configured to accommodate a portion of a tube that is to be joined to the tube received by the other slot 24, 28. This may include each first portion 22a, 26a having a general arcuate or V-shaped profile to facilitate proper positioning (namely, centering) of a tube inserted into the slot 24, 28.

When the upper jaw 18 of the first carriage 14 is in its closed condition (FIG. 1), it covers or overlays tubes received within the slots 24 and 28 to retain the tubes in position during a sterile connection procedure. The illustrated upper jaw 18 includes a latch 30 that is configured to engage a pin 32 of the lower jaw 20 when the upper jaw 18 is in the closed condition. Such an arrangement prevents inadvertent movement of the upper jaw 18 from the closed condition to the open condition (of FIGS. 2-4), though it should be understood that other locking arrangements (e.g., a magnetic interlock) may be employed without departing from the scope of the present disclosure.

The second carriage 16 is similarly configured to the first carriage 14, with an upper jaw 34 that may be configured in accordance with the foregoing description of the upper jaw 18 of the first carriage 14 and a lower jaw 36 that may be configured in accordance with the foregoing description of the lower jaw 20 of the first carriage 14.

As will be described in greater detail, the second carriage 16 is configured to move proximally and distally with respect to the first carriage 14 (and with respect to the housing 12), but in an initial or default position, the second carriage 16 is positioned with a second portion 22b of the proximal slot 24 (which is defined by the lower jaw 36 of the second carriage 16) aligned with the first portion 22a of the proximal slot 24 and a second portion 26b of the distal slot 28 (which is defined by the lower jaw 36 of the second carriage 16) aligned with the first portion 26a of the distal slot 28. With the second carriage 16 in such an initial or default position (and the upper jaws 18 and 34 in their open conditions), a proximal tube P may be inserted into the proximal slot 24, with the proximal tube P being partially received by the first portion 22a of the proximal slot 24 (defined by the lower jaw 20 of the first carriage 14) and partially received by the second portion 22b of the proximal slot 24 (defined by the lower jaw 36 of the second carriage 16). Similarly, a distal tube D may be inserted into the distal slot 28, with the proximal tube P being partially received by the first portion 26a of the distal slot 28 (defined by the lower jaw 20 of the first carriage 14) and partially received by the second portion 26b of the distal slot 28 (defined by the lower jaw 36 of the second carriage 16). The proximal and distal tubes P and D are mounted to the sterile connection device 10 in opposing orientations, with a (typically sealed) end of one of the tubes P, D positioned closer to the first carriage 14 and a (typically sealed) end of the other one of the tubes P, D positioned closer to the second carriage 16. To that end, the upper surface or face of the housing 12 may be provided with indicia 38a and 38b, which indicate the positions and orientations into which the tubes P and D are to be placed at the beginning of a sterile connection procedure.

In addition to the carriages 14 and 16, the sterile connection device 10 also includes a blade handling assembly 40 (FIGS. 4-6) incorporated into the housing 12. The blade handling assembly 40 may be differently configured without departing from the scope of the present disclosure, but in any case is configured to move a solid cutting blade 42 (FIG. 7) into different positions within the housing 12 during the course of a sterile connection procedure. In the illustrated embodiment, the blade handling assembly 40 includes a first linear drive motor 44 (FIGS. 4-6), which is configured to enable movement in proximal and distal directions. As will be described in greater detail, the first linear drive motor 44 is actuated to move a blade 42 into position to be heated, along with optionally moving the second carriage 16 in proximal and distal directions. While a linear drive motor is illustrated, it should be understood that other mechanisms may be provided to effect proximal and distal movement of one or more components of the sterile connection device 10 (including a blade 42) relative to the housing 12.

The illustrated blade handling assembly 40 includes a second linear drive motor 46 (FIG. 6), which is configured to enable movement in upward and downward directions within the housing 12 during the course of a sterile connection procedure. As will be described in greater detail, the second linear drive motor 46 is actuated to move the blade 42 (after is has been heated) vertically into and out of a cutting position. While a linear drive motor is illustrated, it should be understood that other mechanisms may be provided to effect vertical movement of one or more components of the sterile connection device 12 (including a blade 42) relative to the housing 10.

Regardless of the particular configuration of the blade handling assembly 40, it is configured to move a blade from a dispensing position within the housing 12 to an intermediate position (where the blade is heated) and then to a cutting position (to cut the two tubes P and D received within the proximal and distal slots 24 and 28). The blade handling assembly 40 may move a blade into additional positions (e.g., a disposal position, which will be described herein) without departing from the scope of the present disclosure.

In the illustrated embodiment, the dispensing position coincides with the position from which a blade 42 is dispensed from of a blade cartridge 48 (FIGS. 8 and 9). While the sterile connection device 10 is configured as a durable, reusable item, the blades 42 (and, typically the blade cartridge 48) are configured as single-use, disposable items. The illustrated blades 42 are configured as flat or planar wafers formed of a single material or blend of materials (e.g., solid metal, such as copper), in contrast to the multi-layer cutting elements of other sterile connection devices. The blade 42 of FIG. 7 is shown as being substantially rectangular, but it should be understood that the shape of the blade 42 may vary without departing from the scope of the present disclosure. It will be appreciated that, on account of the blade 42 being provided as a disposable, single-use item, it is advantageous for it have a simple and inexpensive configuration, rather than a more complicated and expensive configuration.

The illustrated housing 12 defines a slot or cavity configured to at least partially receive a blade cartridge 48. One end 50 of the blade cartridge 48 includes an opening from which the blades 42 are individually dispensed. As best shown in FIG. 5, the open end 50 of the blade cartridge 48 is oriented adjacent to the first linear drive motor 44 of the blade handling assembly 40. The first linear drive motor 44 is driven in a first or forward direction to move a pusher 52 in a proximal direction so as to contact a blade 42 positioned at the open end 50 of the blade cartridge 48 and move the blade 42 proximally and directly to an intermediate position between and beneath the first and second carriages 14 and 16. The illustrated blade cartridge 48 is spring-loaded, such that dispensing one blade 42 from the open end 50 will cause one or more springs disposed within the blade cartridge 48 to press a subsequent blade 42 into position at the open end 50, where it is ready to be dispensed for a subsequent sterile connection procedure. Once the blade cartridge 48 has been emptied (which may be determined by a sensor of the sterile connection device 10, for example), it may be removed and replaced with a fully loaded blade cartridge 48. Alternatively, the blade cartridge 48 may be removed, refilled with blades 42, and then mounted back into the housing 12.

In the intermediate position, the solid cutting blade 42 is heated by a blade heating assembly 54 incorporated into the housing 12. The illustrated blade heating assembly 54 includes a heating element 56 and a thermocouple 58 (which are both shown in FIG. 5), along with a temperature controller 60 (FIG. 4). The heating element 56 may be variously configured without departing from the scope of the present disclosure, but in any case is configured to at least partially receive and/or support the solid cutting blade 42 in the intermediate position. The heating element 56 applies heat to the blade 42 prior to the blade 42 (and, optionally, the heating element 56 as well) being moved from the intermediate position to the cutting position (e.g., in an upward direction by the second linear drive motor 46), In an exemplary embodiment, the heating element 56 is configured as a ceramic heater having one or more plates that each contact or are positioned directly adjacent to at least a portion of the blade 42 to heat at least a portion of the blade 42 by conductive heating (as opposed to resistive heating, which is employed when a cutting element includes a resistive circuit layer), In the illustrated embodiment, the upper edge of the blade 42 is brought into contact with the tubes P and Ira to cut the tubes P and D, such that it is advantageous for the heating element 56 to be configured to apply heat to at least part of the upper edge of the blade 42. However, as will be described in greater detail, the cut end of one of the tubes P, is moved along the adjacent face of the blade 42 prior to joining the cut ends, so it may be advantageous for a larger portion of the blade 42 (which may include substantially the entire blade 42) to be heated.

The manner in which the heating element 56 is itself heated depends upon the particular configuration of the blade heating assembly 54. For example, in the exemplary embodiment in which the heating element 56 is configured as a ceramic heater, the one or more ceramic plates of the heating element 56 are heated by application of electricity to the plate(s) by the temperature controller 60. The temperature controller 60 may be variously configured without departing from the scope of the present disclosure, with the temperature controller 60 being of the type marketed as the E5DC temperature controller by Omron Corporation of Kyoto, Japan in an exemplary embodiment.

The illustrated heating element 56 includes an internal thermocouple 58 that is electrically coupled to the temperature controller 60. The thermocouple 58 produces a voltage that is dependent upon its temperature (which is dependent upon the temperature of the associated heating element 56), with the voltage being delivered to the temperature controller 60. Upon the temperature controller 60 receiving a voltage that is indicative of a target temperature (which is approximately 300° C. in an exemplary embodiment), the temperature controller 60 transmits a signal to a system controller 62 (FIGS. 4 and 6). The system controller 62 uses the signal from the temperature controller 60 to determine when the blade 42 has been sufficiently heated. This may include the system controller 62 determining that the blade 42 has been sufficiently heated upon receiving the signal from the temperature controller 60 or the system controller 62 making that determination at some later time (e.g., after a predetermined amount of time). Notably, in this embodiment, the temperature of the blade 42 itself is not monitored, but rather only the temperature of the heating element 56. In other embodiments, the temperature of the blade 42 itself may be monitored, though monitoring only the temperature of the heating element 56 may be sufficient to determine the temperature of the blade 42, particularly when a simple blade (e.g., a solid copper blade) is employed, on account of the blade 42 being heated to a predictable temperature upon application of a particular level of heat for a particular amount of time.

As for the system controller 62, it may be variously configured without departing from the scope of the present disclosure, provided that it is configured to coordinate the various tasks carried out by the components of the sterile connection device 10 during a sterile connection procedure. In one embodiment, the system controller 62 may include a microprocessor (which, in fact may include multiple physical and/or virtual processors). According to other embodiments, the system controller 62 may include one or more electrical circuits designed to carry out the actions described herein. In fact, the system controller 62 may include a microprocessor and other circuits or circuitry. In addition, the system controller 62 may include one or more memories. The instructions by which the microprocessor is programmed may be stored on the memory associated with the microprocessor, which memory/memories may include one or more tangible non-transitory computer readable memories, having computer executable instructions stored thereon, which when executed by the microprocessor, may cause the microprocessor to carry out one or more actions as described herein.

Turning now to an exemplary sterile connection procedure, with the upper jaws 18 and 34 in their open condition (as in FIG. 2) an operator places two tubes P and D into the proximal and distal slots 24 and 28 defined by the lower jaws 20 and 36 of the carriages 14 and 16. The (typically sealed) end of the proximal tube P is positioned adjacent to the first carriage 14, while the (typically sealed) end of the distal tube D is positioned adjacent to the second carriage 16, as shown in FIG. 4. Notably, the tubes P and D may have different outer and inner diameters (within an allowable range), rather than necessarily having the same outer and inner diameters.

With the tubes P and D in place, the operator moves the upper jaws 18 and 34 from their open condition to their closed condition (FIG. 1). The upper jaws 18 and 34 may be independently movable between their open and closed conditions or may be configured to move together from the open condition to the closed condition and/or from the closed condition to the open condition. As described above, in their closed conditions, the upper jaws 18 and 34 cover the lower jaws 20 and 36 and secure the tubes P and D within the carriages 14 and 16.

In the illustrated embodiment, a tubing clamp 64 is configured to contact and compress the tubes P and D at a position between the first and second portions of the proximal and distal slots 24 and 28 when the upper jaws 18 and 34 are in the closed condition. By compressing the tubes P and D, the tubing clamp 64 moves any liquid away from the site at which the tubing clamp 64 engages the tubes P and D. As will be described in greater detail, this site corresponds to the location at which the tubes P and D are cut by the heated blade 42, such that the tubing clamp 64 serves to clear liquid from the location at which the tubes P and D are cut. By clearing liquid from this location, it becomes possible to connect and join two tubes when at least one of them contains a liquid. Thus, the inclusion of a tubing clamp 64 allows for a "dry-to-dry" connection (in which neither tube P, D contains a liquid), a "dry-to-wet" connection (in which one tube P, D contains a liquid), and a "wet-to-wet" connection (in which both tubes P and D contain a liquid).

The tubing clamp 64 may be variously configured without departing from the scope of the present disclosure. In one embodiment, the tubing clamp 64 is associated with one or both of the upper jaws 18 and 34, such that movement of the associated upper jaw(s) 18, 34 between open and closed conditions will cause similar movement of the tubing clamp 64. In such a configuration, moving the upper jaws 18 and 34 to their closed condition will move the tubing clamp 64 into contact with the tubes P and D. The tubing clamp 64 may be formed of a metallic material or some other generally rigid material (to ensure that the tubing clamp 64 will compress the tubes P and D when the tubing clamp 64 is moved into contact with the tubes P and D), with the tubing clamp 64 being spring-loaded to control the amount of force applied to the tubes P and D by the tubing clamp 64.

With the upper jaws 18 and 34 in their closed condition, the operator presses a "start" button 66 to continue the sterile connection procedure. In one embodiment, a solid cutting blade 42 is already positioned at the intermediate position (received by the heating element 56 and ready to be heated) when the "start" button 66 is pressed. In this case, pressing the "start" button 66 causes the system controller 62 to command the blade heating assembly 54 to heat the blade 42 to a desired temperature (which may be estimated based on the temperature of the heating element 56 of the blade heating assembly 54, as explained above). If a blade 42 is not present in the intermediate position (as determined by a sensor, for example), pressing the "start" button 66 causes the system controller 62 to command the blade handling assembly 40 to move a blade 42 from the blade cartridge 48 to the intermediate position (e.g., by action of the first linear drive motor 44), followed by the system controller 62 commanding the blade heating assembly 54 to heat the blade 42 to a target temperature.

Upon the blade 42 reaching the target temperature (e.g., as determined by the system controller 62, based upon a signal received from the temperature controller 60), the heated blade 42 is moved from the intermediate position to the cutting position. In the illustrated embodiment, this movement is in the upward direction and carried out by actuation of the second linear drive motor 46 of the blade handling assembly 40. The heated blade 42 presses against the tubes P and D, which are in turn pressed against the tubing clamp 64. The tubing clamp 64 may remain in position while the heated blade 42 presses against the tubes P and D or may be moved by the heated blade 42 (and/or the heating element 56, if the heating element 56 moves to the cutting position with the heated blade 42). In one embodiment, the tubing clamp 64 is moved from its lowered position (which corresponds to the closed condition of the upper jaws 18 and 34) to a raised position by the heated blade 42 and/or the heating element 56 as the blade 42 cuts the tubes P and D, with the tubing clamp 64 being locked into the raised position by a spring 68 moving a latching mechanism 70 into place, or the like.

When the blade 42 has cut through the tubes P and D, the second carriage 16 is moved distally with respect to the first carriage 14 and with respect to the blade 42 (which remains in its cutting position). This movement draws the cut end of the proximal tube P positioned within the second portion 22b of the proximal slot 24 along the heated blade 42, into alignment with the cut end of the distal tube positioned within the first portion 26a of the distal slot 28 (FIG. 5). The second carriage 16 may be moved by any suitable mechanism, with the second carriage 16 being moved in the distal direction by the first linear drive motor 44 as the first linear drive motor 44 moves distally into position to deliver a subsequent blade 42 to the heating element 56, in an exemplary embodiment. A spring 72 (FIG. 6) may also (or alternatively) be employed to cause this distal movement of the second carriage 16.

With the cut ends of the tubes P and 0 so aligned, the system controller 62 commands the blade handling assembly 40 to move the blade 42 back to the intermediate position (e.g., by actuating the second linear drive motor 46 in reverse to lower the heated blade 42) and then commands the first carriage 14 to be moved laterally toward the second carriage 16 so as to bring the cut ends of the tubes P and D into contact with each other. This movement may be carried out by any suitable mechanism, such as (for example) a spring 74 (FIG. 5) pressing the first carriage 16 toward the second carriage 16 or a third linear drive motor (not illustrated) moving the first carriage 14 toward the second carriage 16.

The cut ends of the tubes P and D are pressed together for a predetermined amount of time to create a joint and cool, after which time the system controller 62 advances to the next stage of the procedure. In this stage, the operator is notified that the tubes P and Q have been sterilely connected to define a joined tube J (FIGS. 3 and 6). This notification may be provided in the form of an audible alert (e.g., an alarm) and/or a visual alert (e.g., a flashing light or an icon shown on a screen), for example. At this time, the system controller 62 unlocks the upper jaws 18 and 34 (if they are locked into their closed condition), which allows the operator to move the upper jaws 18 and 34 back into their open condition and then remove the joined tube J from the lower jaws 20 and 36 of the carriages 14 and 16 (along with the cut-off ends of the tubes P and D, which may be discarded). If required, the operator may manipulate the joined tube to ensure that the joint is secure and open for fluid flow (e.g., by pinching the joint).

At the end of the procedure, the operator presses a "reset" button 76 to reset the sterile connection device 10. Pressing the "reset" button 76 causes the blade handling assembly 40 to move a blade 42 from the blade cartridge 48 to the heating element 56 in the intermediate position, which presses the heated blade 42 that was used in the just-completed procedure out of the heating element 56 and into a disposal receptacle 78. The disposal receptacle 78 may be differently configured without departing from the scope of the present disclosure, with the illustrated disposal receptacle 78 being configured as a drawer positioned at the front or proximal face of the housing 12 and including a door or access 80 that may be opened to allow spent blades 42 to be removed from the disposal receptacle 78.

The system controller 62 also commands the first and second carriages 14 and 16 to return to their default or initial positions (namely, by moving the first carriage 14 laterally away from the second carriage 16, while moving the second carriage 16 in a proximal direction). In one embodiment, the first linear drive motor 42 is responsible for simultaneously moving the second carriage 16 to its original position and moving a blade 42 from the blade cartridge 48 to the intermediate position, though it is within the scope of the present disclosure for different mechanisms to be employed.

FIGS. 10-13 illustrate another exemplary configuration of a sterile connection device 100 according to the present disclosure. The sterile connection device 100 is similarly configured to the sterile connection device 10, except that it is configured to simultaneously join two pairs of sealed tubes, rather than joining only a single pair of sealed tubes. To allow for two pairs of tubes to be joined, the sterile connection device 100 has modified carriages 102 and 104. Whereas the carriages 14 and 16 of sterile connection device 10 (when aligned, as in FIG. 2) combine to define a pair of parallel slots 24 and 28, lower jaws 106 and 108 of carriages 102 and 104 of sterile connection device 100 combine to define four pairs of parallel slots 110, 112, 114, and 116. The individual slots 110, 112, 114, and 116 may be similarly configured to the previously described slots 24 and 28, with the lower jaw 106 of the first carriage 102 forming a first portion of each slot and the lower jaw 108 of the second carriage 104 forming an aligned second portion of the corresponding slot. More particularly, the lower jaw 106 of the first carriage 102 defines a first portion 118a of first slot 110, a first portion 120a of second slot 112, a first portion 122a of third slot 114, and a first portion 124a of fourth slot 116, while the lower jaw 108 of the second carriage 104 defines a second portion 118b of the first slot 110, a second portion 120b of the second slot 112, a second portion 122b of the third slot 114, and a second portion 124b of the fourth slot 116.

Figure 10:
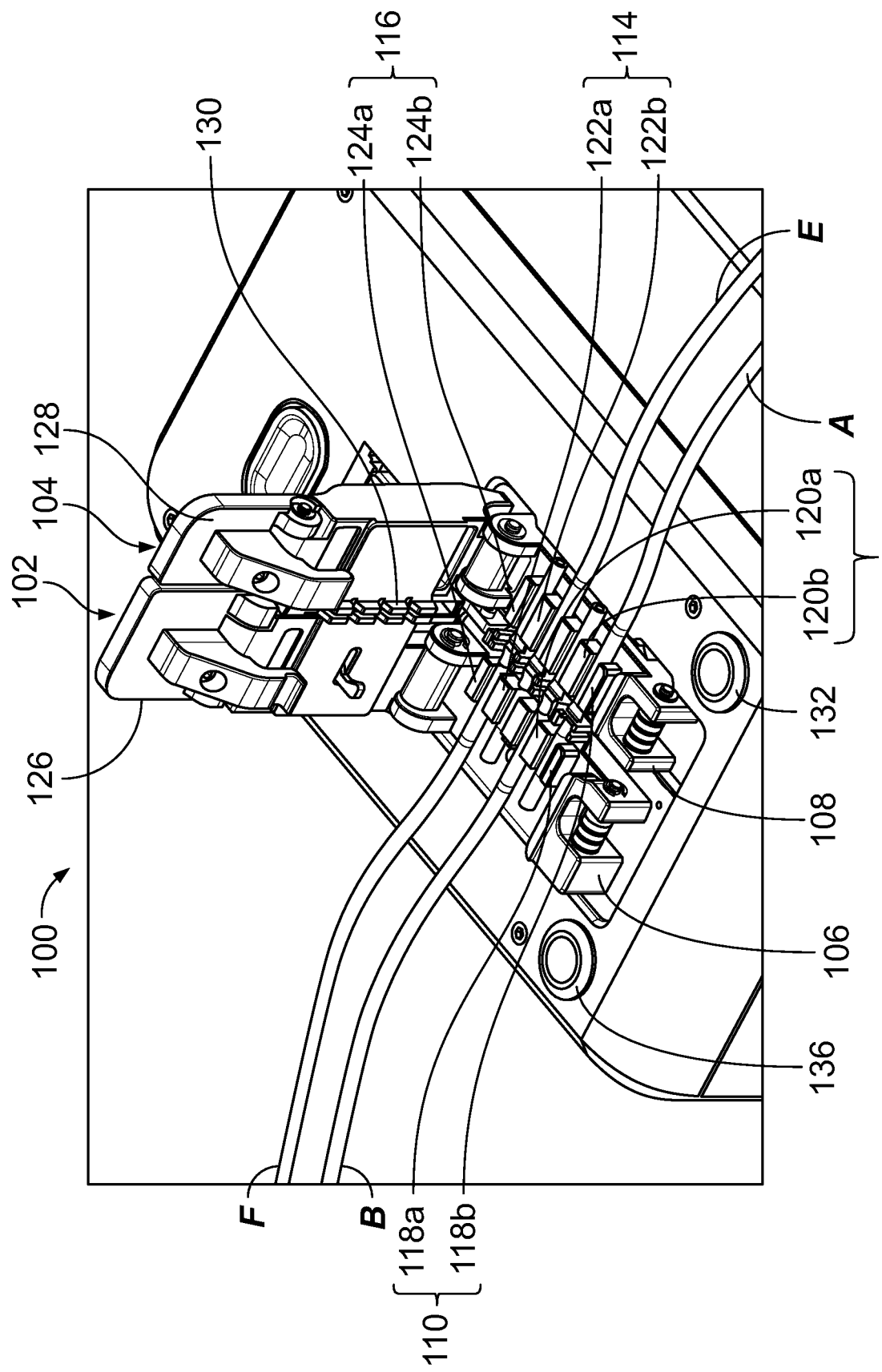
FIG. 10 is a perspective view of another exemplary embodiment of a sterile connection device according to the present disclosure, with first and second carriages of the device aligned and upper jaws of the carriages in an open condition.
Figure 11:
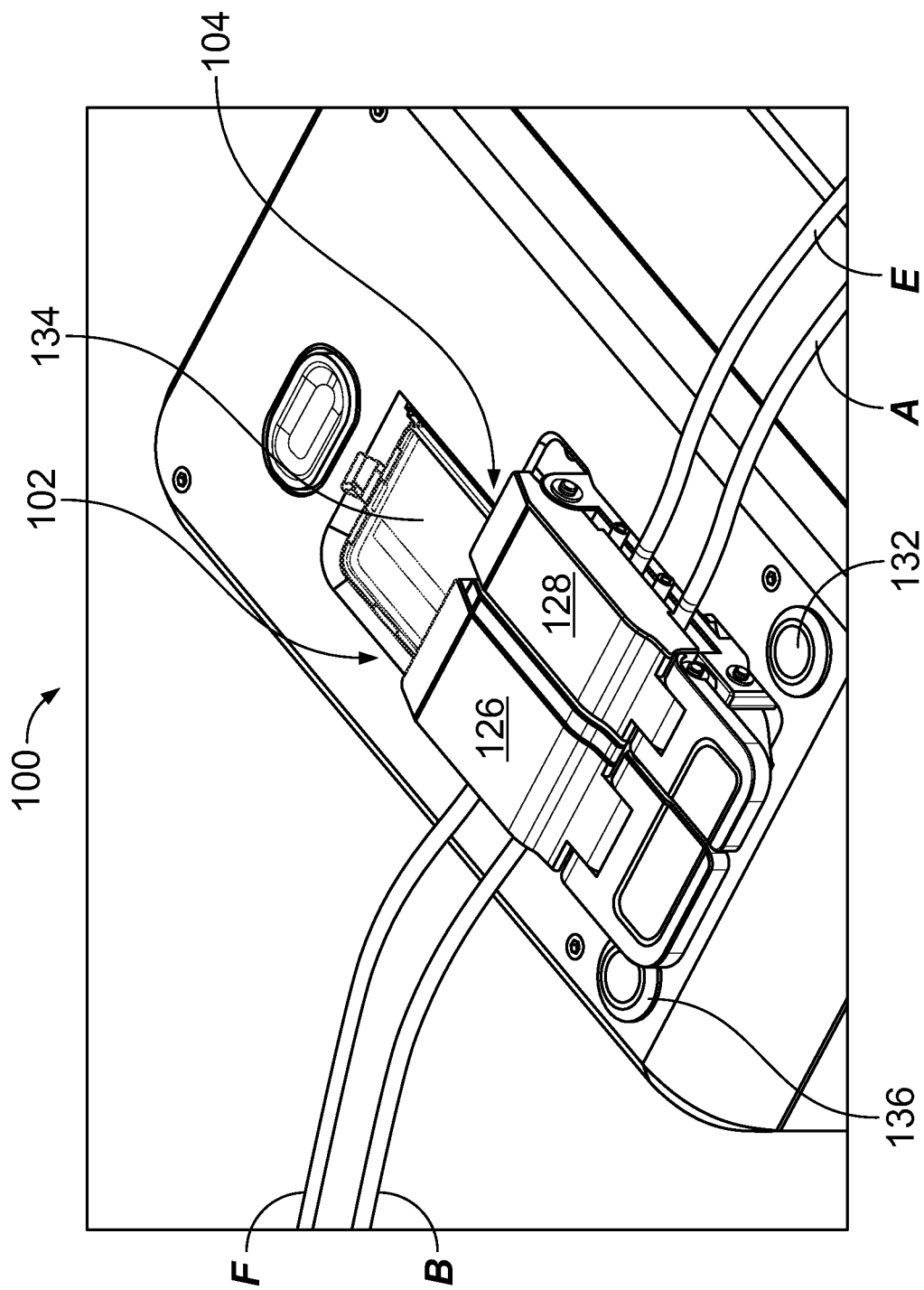
FIG. 11 is a perspective view of the sterile connection device of FIG. 10, with the upper jaws of the first and second carriages in a closed condition.

As shown in FIG. 10, a first tube "A" may be inserted into the first slot 110, with the first tube A being partially received by the first portion 118a of the first slot 110 (defined by the lower jaw 106 of the first carriage 102) and partially received by the second portion 118b of the first slot 110 (defined by the lower jaw 108 of the second carriage 104). Similarly, a second tube "B" may be inserted into the second slot 112, with a third tube "E" inserted into the third slot 114 and a fourth tube "F" inserted into the fourth slot 116. The first and second tubes A and B (which are to be joined together) are mounted to the sterile connection device 100 in opposing orientations, with a (typically sealed) end of one of the tubes A, B positioned closer to the first carriage 102 and a (typically sealed) end of the other one of the tubes A, B positioned closer to the second carriage 104. The third and fourth tubes E and F (which are to be joined together) are similarly mounted to the sterile connection device 100 in opposing orientations, as can be seen in FIG. 10.

With the tubes in place, the operator moves the respective upper jaws 126 and 128 of the first and second carriages 102 and 104 from their open condition (FIG. 10) to their closed condition (FIG. 11) to secure the tubes within the carriages 102 and 104. If provided (as in the illustrated embodiment), a tubing clamp 130 contacts and compresses the tubes at a position between the first and second portions of each slot when the upper jaws 126 and 128 are in the closed condition to move any liquid away from the location at which the tubes are to be cut.

With the upper jaws 126 and 128 in their closed condition, the operator presses a "start" button 132 to continue the sterile connection procedure. In one embodiment, a solid cutting blade is already positioned at an intermediate position (received by a heating element and ready to be heated) when the "start" button 132 is pressed. In this case, pressing the "start" button 132 causes the system controller to command a blade heating assembly to heat the blade to a desired temperature. If a blade is not present in the intermediate position (as determined by a sensor, for example), pressing the "start" button 132 causes the system controller to command a blade handling assembly to move a blade from the blade cartridge 134 to the intermediate position, followed by the system controller commanding the blade heating assembly to heat the blade to a target temperature. As the blade is required to cut through four tubes instead of two (as in the embodiment of FIGS. 1-6), each blade employed by the sterile connection device 100 may be elongated compared to the blades 42 employed by the sterile connection device 10. Alternatively, rather than providing one elongated blade, it is also within the scope of the present disclosure for a plurality of blades (which may be similarly or differently configured) to be used when cutting the four tubes.

Figure 12:
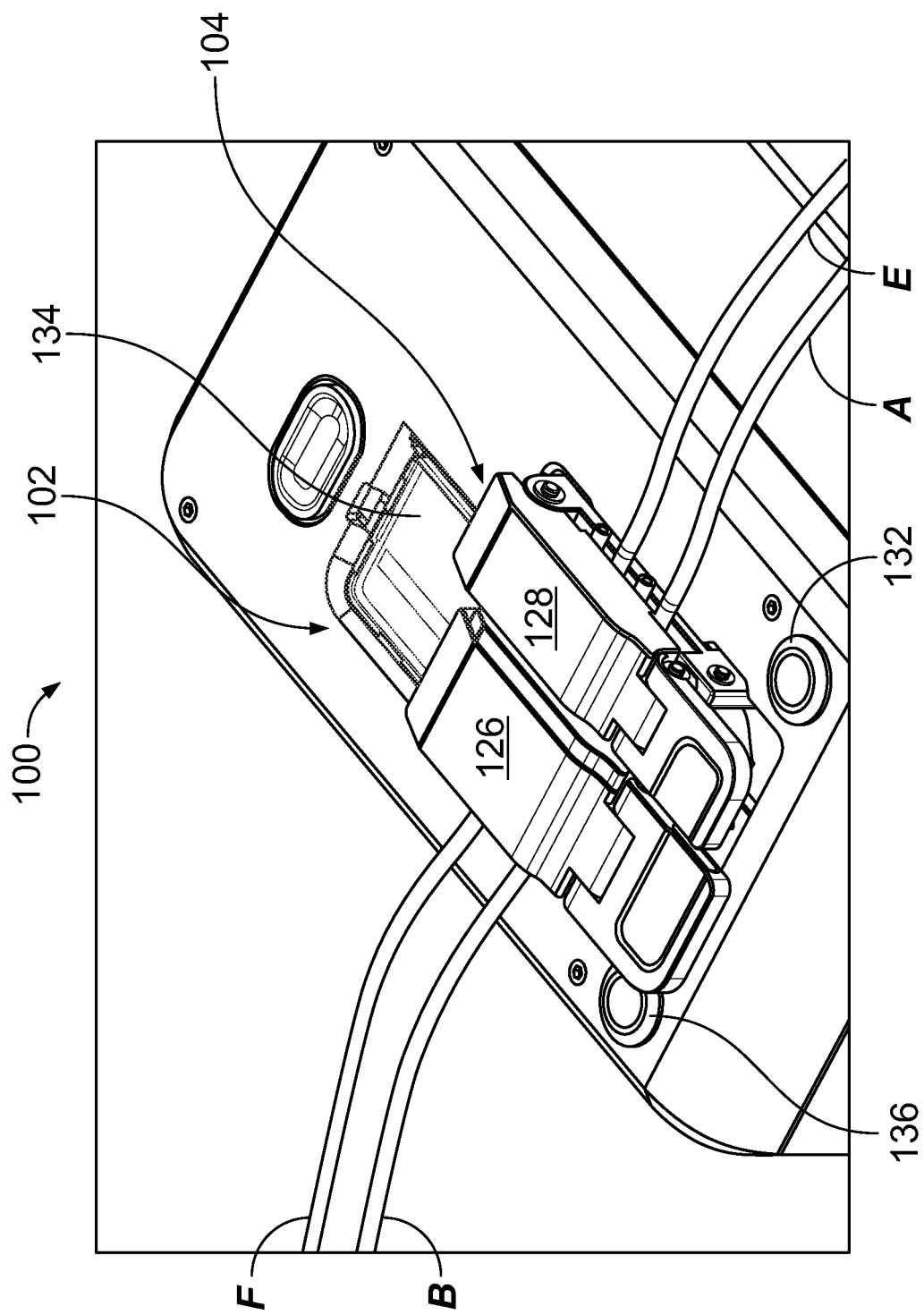
FIG. 12 is a perspective view of the sterile connection device of FIG. 10, with the first and second carriages out of alignment and the upper jaws in their closed condition.
Figure 13:
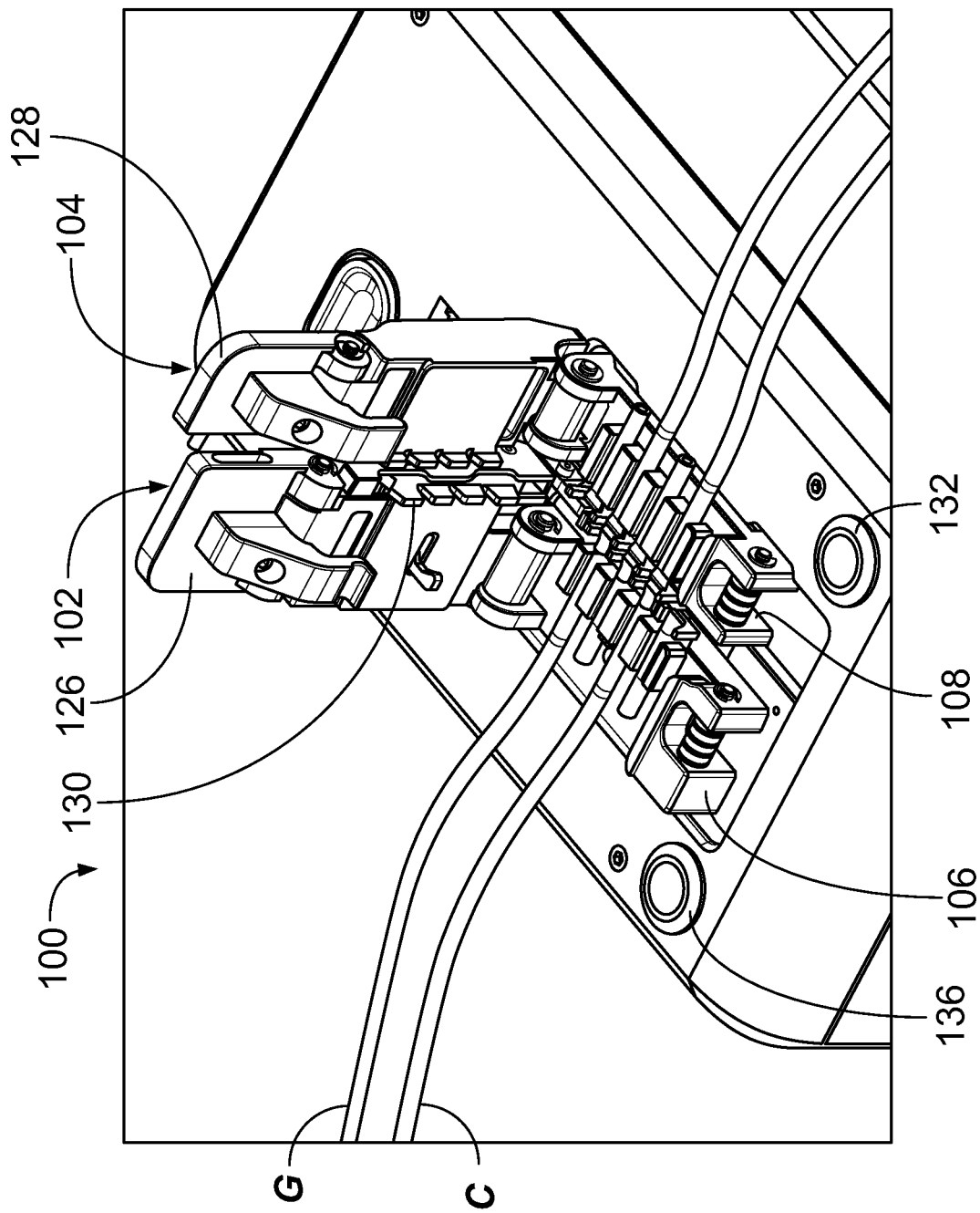
FIG. 13 is a perspective view of the sterile connection device of FIG. 10, with the first and second carriages out of alignment and the upper jaws in their open condition.

Upon the blade reaching the target temperature, the heated blade is moved from the intermediate position to the cutting position by the blade handling assembly. The heated blade presses against the tubes, which are in turn pressed against the tubing clamp 130 to cut through the tubes. When the blade has cut through the tubes, the second carriage 104 is moved distally with respect to the first carriage 102 and with respect to the blade (which remains in its cutting position). This movement draws the cut ends of the first tube A and the third tube E along the heated blade, into alignment with the cut ends of the second tube B and the fourth tube F, respectively (FIG. 12).

With the cut ends of the tubes so aligned, the system controller commands the blade handling assembly to move the blade back to the intermediate position and then commands the first carriage 102 to be moved laterally toward the second carriage 104 so as to bring the aligned cut ends of the two pairs of tubes into contact with each other. The cut ends of the first and second tubes A and B and of the third and fourth tubes E and F are pressed together for a predetermined amount of time to create a joint and cool, after which the system controller advances to the next stage of the procedure.

In the next stage, the operator is notified that the first and second tubes A and B have been sterilely connected to define a first joined tube "C," with the third and fourth tube E and F being sterilely connected to define a second joined tube "G." At this time, the system controller unlocks the upper jaws 126 and 128 (if they are locked into their closed condition), which allows the operator to move the upper jaws 126 and 128 back into their open condition (FIG. 13) and then remove the joined tubes C and G from the lower jaws 106 and 108 of the carriages 102 and 104 (along with the cut-off ends of the tubes, which may be discarded). If required, the operator may manipulate the joined tubes to ensure that the joints are secure and open for fluid flow (e.g., by pinching the joint). At the end of the procedure, the operator presses a "reset" button 136 to reset the sterile connection device 100.

While it will be seen that the sterile connection device 100 of FIGS. 10-13 is particularly suited for simultaneously joining two pairs of tubes, it should be understood that the sterile connection device 100 may also be used to join a single pair of tubes. Additionally, while the sterile connection device 100 is shown as being configured to join one or two pairs of tubes, it should be understood that a sterile connection device may be configured to simultaneously join three or more pairs of tubes by providing suitably configured components (e.g., elongated carriages and blades).

It should again be emphasized that the illustrated sterile connection devices 10 and 100 are merely exemplary and that sterile connection devices according to the present disclosure may be differently configured without departing from the scope of the present disclosure. This may include a sterile connection device having its components differently arranged and/or a sterile connection device including additional components (e.g., a cord for connection to an external power source, a variety of sensors, and/or a touchscreen for use by an operator).

Aspects

Aspect 1. A sterile connection device comprising: a housing; a first carriage including a first lower jaw defining a first portion of a proximal slot configured to receive a portion of a proximal sealed tube and defining a first portion of a distal slot configured to receive a portion of a distal sealed tube, and a first upper jaw configured to move between an open condition spaced away from the first lower jaw and a closed condition positioned adjacent to the first lower jaw; a second carriage positioned laterally of the first carriage and including a second lower jaw defining a second portion of the proximal slot and a second portion of the distal slot, and a second upper jaw configured to move between an open condition spaced away from the second lower jaw and a closed condition positioned adjacent to the second lower jaw; a blade handling assembly configured to move a solid cutting blade into a plurality of positions within the housing; a blade heating assembly; and a system controller configured to execute a sterile connection procedure when proximal and distal tubes are received by the proximal and distal slots and the first and second upper jaws are in the closed conditions, wherein the sterile connection procedure includes controlling the blade heating assembly to heat the solid cutting blade, controlling the blade handling assembly to move the heated blade to a cutting position so as to cut the proximal and distal tubes, controlling the second carriage to move proximally or distally with respect to the first carriage so as to align one of the portions of the proximal slot with one of the portions of the distal slot, controlling the blade handling assembly to advance the heated blade out of the cutting position, and controlling the first carriage to move laterally toward the second carriage so as to press cut ends of the proximal and distal tubes received by the aligned portions of the proximal and distal slots into contact with each other so as to sterilely connect the cut ends and define a joined tube, wherein the solid cutting blade is heated by conductive heating applied by the blade heating assembly.

Aspect 2. The sterile connection device of Aspect 1, wherein the blade heating assembly comprises a ceramic heating element.

Aspect 3. The sterile connection device of any one of the preceding Aspects, wherein the blade heating assembly includes an internal thermocouple configured to measure a temperature of a portion of the blade heating assembly and not a temperature of the solid cutting blade.

Aspect 4. The sterile connection device of Aspect 3, wherein the blade heating assembly includes a temperature controller associated with the internal thermocouple and configured to transmit a signal to the system controller upon determining that the said portion of the blade heating assembly has reached a target temperature, and the system controller is configured to control the blade handling assembly to move the heated blade to the cutting position so as to cut the proximal and distal tubes based at least in part on the signal from the temperature controller.

Aspect 5. The sterile connection device of any one of the preceding Aspects, further comprising a tubing clamp configured to contact and compress the proximal and distal tubes at a position between the first and second portions of the proximal and distal slots when the upper jaws are in the closed conditions.

Aspect 6. The sterile connection device of Aspect 5, wherein the tubing clamp is configured to be contacted and moved by the heating blade from a lowered position to a raised position upon the heated blade being moved to the cutting position by the blade handling assembly.

Aspect 7. The sterile connection device of any one of the preceding Aspects, further comprising a "reset" button configured to be manipulated by an operator, wherein manipulation of the "reset" button instructs the controller to control the blade handling assembly to move the heated blade to a disposal receptacle.

Aspect 8. The sterile connection device of Aspect 7, wherein manipulation of the "reset" button instructs the controller to control the blade handling assembly to move a subsequent solid cutting blade from a blade cartridge directly to an intermediate position between the blade cartridge and the cutting position, with movement of the subsequent solid cutting blade to the intermediate position causing the heated blade to be moved to the disposal receptacle.

Aspect 9. The sterile connection device of any one of the preceding Aspects, wherein the blade handling assembly includes a first linear drive motor configured to advance the solid cutting blade from a blade cartridge directly to an intermediate position between the blade cartridge and the cutting position, with the solid cutting blade being heated by the blade heating assembly in the intermediate position, and a second linear drive motor configured to advance the heated blade from the intermediate position to the cutting position.

Aspect 10. The sterile connection device of Aspect 9, wherein the first linear drive motor is configured to move the solid cutting blade in a direction substantially perpendicular to a direction in which the second linear drive motor is configured to move the heated blade.

Aspect 11. The sterile connection device of any one of Aspects 9-10, wherein the first linear drive motor is configured to move from the intermediate position toward the blade cartridge so as to cause the second carriage to move proximally or distally with respect to the first carriage so as to align said one of the portions of the proximal slot with said one of the portions of the distal slot.

Aspect 12. The sterile connection device of any one of the preceding Aspects, further comprising a first spring configured to bias the first carriage toward the second carriage, wherein the system controller is configured to control the first carriage to move laterally toward the second carriage by allowing the spring to move the first carriage toward the second carriage.

Aspect 13. The sterile connection device of any one of the preceding Aspects, further comprising a second spring configured to bias the second carriage to move proximally or distally with respect to the first carriage, wherein the system controller is configured to control the second carriage to move proximally or distally with respect to the first carriage by allowing the second spring to move the second carriage proximally or distally with respect to the first carriage.

Aspect 14. The sterile connection device of any one of the preceding Aspects, configured to simultaneously join multiple pairs of tubes.

Aspect 15. The sterile connection device of any one of the preceding Aspects, wherein the solid cutting blade comprises a solid copper blade.

Aspect 16. A sterile connection device comprising: a housing; a first carriage including a first lower jaw defining a first portion of a proximal slot configured to receive a portion of a proximal sealed tube and defining a first portion of a distal slot configured to receive a portion of a distal sealed tube, and a first upper jaw configured to move between an open condition spaced away from the first lower jaw and a closed condition positioned adjacent to the first lower jaw; a second carriage positioned laterally of the first carriage and including a second lower jaw defining a second portion of the proximal slot and a second portion of the distal slot, and a second upper jaw configured to move between an open condition spaced away from the second lower jaw and a closed condition positioned adjacent to the second lower jaw; a blade handling assembly configured to move a solid cutting blade into a plurality of positions within the housing; a blade heating assembly; and a system controller configured to execute a sterile connection procedure when proximal and distal tubes are received by the proximal and distal slots and the first and second upper jaws are in the closed conditions, wherein the sterile connection procedure includes controlling the blade heating assembly to heat the solid cutting blade, controlling the blade handling assembly to move the heated blade to a cutting position so as to cut the proximal and distal tubes, controlling the second carriage to move proximally or distally with respect to the first carriage so as to align one of the portions of the proximal slot with one of the portions of the distal slot, controlling the blade handling assembly to advance the heated blade out of the cutting position, and controlling the first carriage to move laterally toward the second carriage so as to press cut ends of the proximal and distal tubes received by the aligned portions of the proximal and distal slots into contact with each other so as to sterilely connect the cut ends and define a joined tube, wherein the solid cutting blade is heated by a ceramic heating element of the blade heating assembly.

Aspect 17. The sterile connection device of Aspect 16, wherein the blade heating assembly includes an internal thermocouple configured to measure a temperature of a portion of the blade heating assembly and not a temperature of the solid cutting blade.

Aspect 18. The sterile connection device of Aspect 17, wherein the blade heating assembly includes a temperature controller associated with the internal thermocouple and configured to transmit a signal to the system controller upon determining that the said portion of the blade heating assembly has reached a target temperature, and the system controller is configured to control the blade handling assembly to move the heated blade to the cutting position so as to cut the proximal and distal tubes based at least in part on the signal from the temperature controller.

Aspect 19. The sterile connection device of any one of Aspects 16-18, further comprising a tubing clamp configured to contact and compress the proximal and distal tubes at a position between the first and second portions of the proximal and distal slots when the upper jaws are in the closed conditions.

Aspect 20. The sterile connection device of Aspect 19, wherein the tubing clamp is configured to be contacted and moved by the heating blade from a lowered position to a raised position upon the heated blade being moved to the cutting position by the blade handling assembly.

Aspect 21. The sterile connection device of any one of Aspects 16-20, further comprising a "reset" button configured to be manipulated by an operator, wherein manipulation of the "reset" button instructs the controller to control the blade handling assembly to move the heated blade to a disposal receptacle.

Aspect 22. The sterile connection device of Aspect 21, wherein manipulation of the "reset" button instructs the controller to control the blade handling assembly to move a subsequent solid cutting blade from a blade cartridge directly to an intermediate position between the blade cartridge and the cutting position, with movement of the subsequent solid cutting blade to the intermediate position causing the heated blade to be moved to the disposal receptacle.

Aspect 23. The sterile connection device of any one of Aspects 16-22, wherein the blade handling assembly includes a first linear drive motor configured to advance the solid cutting blade from a blade cartridge directly to an intermediate position between the blade cartridge and the cutting position, with the solid cutting blade being heated by the blade heating assembly in the intermediate position, and a second linear drive motor configured to advance the heated blade from the intermediate position to the cutting position.

Aspect 24. The sterile connection device of Aspect 23, wherein the first linear drive motor is configured to move the solid cutting blade in a direction substantially perpendicular to a direction in which the second linear drive motor is configured to move the heated blade.

Aspect 25. The sterile connection device of any one of Aspects 23-24, wherein the first linear drive motor is configured to move from the intermediate position toward the blade cartridge so as to cause the second carriage to move proximally or distally with respect to the first carriage so as to align said one of the portions of the proximal slot with said one of the portions of the distal slot.

Aspect 26. The sterile connection device of any one of Aspects 16-25, further comprising a first spring configured to bias the first carriage toward the second carriage, wherein the system controller is configured to control the first carriage to move laterally toward the second carriage by allowing the spring to move the first carriage toward the second carriage.

Aspect 27. The sterile connection device of any one of Aspects 16-26, further comprising a second spring configured to bias the second carriage to move proximally or distally with respect to the first carriage, wherein the system controller is configured to control the second carriage to move proximally or distally with respect to the first carriage by allowing the second spring to move the second carriage proximally or distally with respect to the first carriage.

Aspect 28. The sterile connection device of any one of Aspects 16-27, configured to simultaneously join multiple pairs of tubes.

Aspect 29. The sterile connection device of any one of Aspects 16-28, wherein the solid cutting blade comprises a solid copper blade.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A sterile connection device comprising:
   a housing;
   a first carriage including
      a first lower jaw defining a first portion of a proximal slot configured to receive a portion of a proximal sealed tube and defining a first portion of a distal slot configured to receive a portion of a distal sealed tube, and
      a first upper jaw configured to move between an open condition spaced away from the first lower jaw and a closed condition positioned adjacent to the first lower jaw;
   a second carriage positioned laterally of the first carriage and including
      a second lower jaw defining a second portion of the proximal slot and a second portion of the distal slot, and
      a second upper jaw configured to move between an open condition spaced away from the second lower jaw and a closed condition positioned adjacent to the second lower jaw;
   a blade handling assembly configured to move a solid cutting blade into a plurality of positions within the housing;
   a blade heating assembly; and
   a system controller configured to execute a sterile connection procedure when proximal and distal tubes are received by the proximal and distal slots and the first and second upper jaws are in the closed conditions, wherein the sterile connection procedure includes
      controlling the blade heating assembly to heat the solid cutting blade,
      controlling the blade handling assembly to move the heated blade away from the blade heating assembly to a cutting position so as to cut the proximal and distal tubes,
      controlling the second carriage to move proximally or distally with respect to the first carriage so as to align one of the portions of the proximal slot with one of the portions of the distal slot,
      controlling the blade handling assembly to advance the heated blade out of the cutting position, and
      controlling the first carriage to move laterally toward the second carriage so as to press cut ends of the proximal and distal tubes received by the aligned portions of the proximal and distal slots into contact with each other so as to sterilely connect the cut ends and define a joined tube, wherein the solid cutting blade is heated by conductive heating applied by the blade heating assembly.

2. The sterile connection device of claim 1, wherein the blade heating assembly includes an internal thermocouple configured to measure a temperature of a portion of the blade heating assembly and not a temperature of the solid cutting blade.

3. The sterile connection device of claim 2, wherein
   the blade heating assembly includes a temperature controller associated with the internal thermocouple and configured to transmit a signal to the system controller upon determining that the said portion of the blade heating assembly has reached a target temperature, and
   the system controller is configured to control the blade handling assembly to move the heated blade to the cutting position so as to cut the proximal and distal tubes based at least in part on the signal from the temperature controller.

4. The sterile connection device of claim 1, further comprising a tubing clamp configured to contact and compress the proximal and distal tubes at a position between the first and second portions of the proximal and distal slots when the upper jaws are in the closed conditions.

5. The sterile connection device of claim 4, wherein the tubing clamp is configured to be contacted and moved by the heated blade from a lowered position to a raised position upon the heated blade being moved to the cutting position by the blade handling assembly.

6. The sterile connection device of claim 1, wherein the blade handling assembly includes
   a first linear drive motor configured to advance the solid cutting blade from a blade cartridge directly to an intermediate position between the blade cartridge and the cutting position, with the solid cutting blade being heated by the blade heating assembly in the intermediate position, and
   a second linear drive motor configured to advance the heated blade from the intermediate position to the cutting position.

7. The sterile connection device of claim 6, wherein the first linear drive motor is configured to move the solid cutting blade in a direction substantially perpendicular to a direction in which the second linear drive motor is configured to move the heated blade.

8. The sterile connection device of claim 6, wherein the first linear drive motor is configured to move from the intermediate position toward the blade cartridge so as to cause the second carriage to move proximally or distally with respect to the first carriage so as to align said one of the portions of the proximal slot with said one of the portions of the distal slot.

9. The sterile connection device of claim 1, configured to simultaneously join multiple pairs of tubes.

10. The sterile connection device of claim 1, wherein the solid cutting blade comprises a solid copper blade.

11. A sterile connection device comprising:
    a housing;
    a first carriage including
       a first lower jaw defining a first portion of a proximal slot configured to receive a portion of a proximal sealed tube and defining a first portion of a distal slot configured to receive a portion of a distal sealed tube, and
       a first upper jaw configured to move between an open condition spaced away from the first lower jaw and a closed condition positioned adjacent to the first lower jaw;
    a second carriage positioned laterally of the first carriage and including a second lower jaw defining a second portion of the proximal slot and a second portion of the distal slot, and a second upper jaw configured to move between an open condition spaced away from the second lower jaw and a closed condition positioned adjacent to the second lower jaw;

a blade handling assembly configured to move a solid cutting blade into a plurality of positions within the housing;

a blade heating assembly; and a system controller configured to execute a sterile connection procedure when proximal and distal tubes are received by the proximal and distal slots and the first and second upper jaws are in the closed conditions, wherein the sterile connection procedure includes controlling the blade heating assembly to heat the solid cutting blade, controlling the blade handling assembly to move the heated blade away from the blade heating assembly to a cutting position so as to cut the proximal and distal tubes, controlling the second carriage to move proximally or distally with respect to the first carriage so as to align one of the portions of the proximal slot with one of the portions of the distal slot, controlling the blade handling assembly to advance the heated blade out of the cutting position, and controlling the first carriage to move laterally toward the second carriage so as to press cut ends of the proximal and distal tubes received by the aligned portions of the proximal and distal slots into contact with each other so as to sterilely connect the cut ends and define a joined tube, wherein the solid cutting blade is heated by a ceramic heating element of the blade heating assembly.

12. The sterile connection device of claim 11, wherein the blade heating assembly includes an internal thermocouple configured to measure a temperature of a portion of the blade heating assembly and not a temperature of the solid cutting blade.

13. The sterile connection device of claim 12, wherein the blade heating assembly includes a temperature controller associated with the internal thermocouple and configured to transmit a signal to the system controller upon determining that the said portion of the blade heating assembly has reached a target temperature, and the system controller is configured to control the blade handling assembly to move the heated blade to the cutting position so as to cut the proximal and distal tubes based at least in part on the signal from the temperature controller.

14. The sterile connection device of claim 11, further comprising a tubing clamp configured to contact and compress the proximal and distal tubes at a position between the first and second portions of the proximal and distal slots when the upper jaws are in the closed conditions.

15. The sterile connection device of claim 14, wherein the tubing clamp is configured to be contacted and moved by the heating blade from a lowered position to a raised position upon the heated blade being moved to the cutting position by the blade handling assembly.

16. The sterile connection device of claim 11, wherein the blade handling assembly includes a first linear drive motor configured to advance the solid cutting blade from a blade cartridge directly to an intermediate position between the blade cartridge and the cutting position, with the solid cutting blade being heated by the blade heating assembly in the intermediate position, and a second linear drive motor configured to advance the heated blade from the intermediate position to the cutting position.

17. The sterile connection device of claim 16, wherein the first linear drive motor is configured to move the solid cutting blade in a direction substantially perpendicular to a direction in which the second linear drive motor is configured to move the heated blade.

18. The sterile connection device of claim 16, wherein the first linear drive motor is configured to move from the intermediate position toward the blade cartridge so as to cause the second carriage to move proximally or distally with respect to the first carriage so as to align said one of the portions of the proximal slot with said one of the portions of the distal slot.

19. The sterile connection device of claim 11, configured to simultaneously join multiple pairs of tubes.

20. The sterile connection device of claim 11, wherein the solid cutting blade comprises a solid copper blade.

* * * * *